(12) United States Patent
Floyd et al.

(10) Patent No.: US 6,717,664 B2
(45) Date of Patent: Apr. 6, 2004

(54) SYSTEM AND METHOD FOR INSPECTING A BEAM USING MICRO FIBER-OPTIC TECHNOLOGY

(75) Inventors: Joseph F. Floyd, University Place, WA (US); John R. Linn, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 10/171,342

(22) Filed: Jun. 14, 2002

(65) Prior Publication Data

US 2003/0231301 A1 Dec. 18, 2003

(51) Int. Cl.⁷ .............................................. G01N 21/00
(52) U.S. Cl. .................. 356/237.1; 356/237.2
(58) Field of Search .................. 356/237.1–237.3, 356/237.6; 267/141.7, 152, 293; 15/304, 324, 339, 414, 415.1

(56) References Cited

U.S. PATENT DOCUMENTS

| | | | | |
|---|---|---|---|---|
| 4,659,195 A | * | 4/1987 | D'Amelio et al. | 359/503 |
| 4,837,615 A | * | 6/1989 | Boshier | 348/82 |
| 5,271,581 A | * | 12/1993 | Irish | 244/129.3 |
| 5,311,639 A | * | 5/1994 | Boshier | 15/324 |
| 5,644,394 A | * | 7/1997 | Owens | 356/241.5 |
| 5,755,163 A | * | 5/1998 | Coats | 108/53.5 |
| 5,876,024 A | * | 3/1999 | Hain | 267/141.4 |
| 6,158,690 A | * | 12/2000 | Wadey et al. | 244/17.27 |

* cited by examiner

Primary Examiner—Michael P. Stafira
(74) Attorney, Agent, or Firm—Harness Dickey & Pierce P.L.C.

(57) ABSTRACT

A system for inspecting a surface of a beam covered by at least one structure. The system includes at least one nut clip attached to the beam used to couple the structure to the beam, and at least one spacer inserted between the beam and the structure for creating a gap between the structure and the beam. A micro fiber-optic borescope is used to view the surface of the beam covered by the structure without removing the structure. The surface is viewed by inserting a micro fiber-optic thread of the borescope into the gap. The system eliminates the need for costly and time consuming disassembly and removal of components mounted on the structure before an inspection of the condition of the beam can be made.

21 Claims, 2 Drawing Sheets

SYSTEM AND METHOD FOR INSPECTING A BEAM USING MICRO FIBER-OPTIC TECHNOLOGY

FIELD OF INVENTION

The invention relates generally to the use of micro fiber-optic technology to inspect a beam surface. More specifically, the invention relates to inspecting a concealed surface of a beam by inserting a micro fiber-optic thread of a micro fiber-optic borescope between the beam and a structure concealing the surface.

BACKGROUND OF THE INVENTION

Inspection of a beam, such as a floor beam of an aircraft, for corrosion and/or cracks, usually requires the removal of whatever structure is mounted on the beam, for example floor panels. If a complex structure, such as an aircraft lavatory, is mounted to the beam, removal of such a structure in order to inspect the concealed surface of the beam is difficult, labor intensive, and very costly.

For example, maintenance programs for a commercial airline aircraft typically require heavy maintenance checks to be performed between every 5 to 7 years. During heavy maintenance checks, the floor structure is inspected for corrosion damage by completely removing everything that is mounted to the floor beams, including floor panels and all structures above the floor panels. Corrosion damage to the aluminum floor beams of an aircraft most frequently happens around 'wet' areas, near entry doors and under lavatories and galleys, which can leak fluids. Such corrosion damage is most frequently found on the upper surface of the aluminum floor beam, and particularly around the fastener holes used to attach the floor panels to the floor beams.

In order to inspect the upper surface of the floor beam, the airline inspection crew must remove the lavatories, seats, galleys, closets, etc., and then remove the floor panels. On the average, removing one galley, taking up the floor panels, inspecting the beams, replacing beams or treating the beams with a corrosion inhibiting compound, and then replacing the floor and galley, can require over 600 hours of labor per galley (or lavatory, etc.), thereby making such an inspection/repair process very costly.

Therefore, it would be highly desirable to be able to inspect a concealed surface of a beam, such as an aircraft floor beam, without having to remove the structure mounted to the beam.

BRIEF SUMMARY OF THE INVENTION

In one preferred embodiment, the present invention is directed to a system for inspecting a surface of a beam covered by at least one structure. The system includes at least one nut clip attached to the beam used to couple the structure to the beam and create a gap between the structure and the beam. Additionally, the system includes a micro fiber-optic borescope used to view the surface of the beam covered by the structure without removing the structure. Alternatively, the system also includes at least one spacer inserted between the beam and the structure for creating the gap between the structure and the beam. The surface is viewed by inserting a micro fiber-optic thread of the borescope into the gap.

The present invention also involves a method for inspecting a surface of a beam covered by at least one structure. The method includes attaching the structure to the beam utilizing a nut clip having an upper leg and a lower leg, wherein the upper leg is shorter than the lower leg. The method also includes creating a gap between the beam and the structure utilizing the upper leg of the nut clip, and viewing the beam surface covered by the structure utilizing a micro fiber-optic borescope. Alternatively, the method includes inserting at least one spacer between the beam and the structure, thereby creating the gap between the beam and the structure.

In another preferred embodiment an apparatus is provided for securing panels over an upper surface of a support beam to permit inspection of the beam upper surface. The apparatus includes a plurality of nut clips attached to the beam for mounting the panels to the beam, and at least one spacer inserted between the beam upper surface and the panel. The spacer creates a gap between the beam upper surface and the panel. The gap is sufficient to introduce a micro fiber-optic thread of a micro fiber-optic borescope used to view the covered surface of the beam.

BRIEF DESCRIPTION OF THE DRAWINGS

The present invention will become more fully understood from the detailed description and accompanying drawings, wherein.

DETAILED DESCRIPTION OF THE INVENTION

Although the preferred embodiments are described below in terms of inspecting floor beams of an aircraft, the invention should not be so narrowly construed or limited as to apply only to aircraft. It is envisioned that the invention is applicable to the inspection of a concealed surface of any beam, whether the beam be in an aircraft, bus, ship, building or any other structure.

Figure 1:
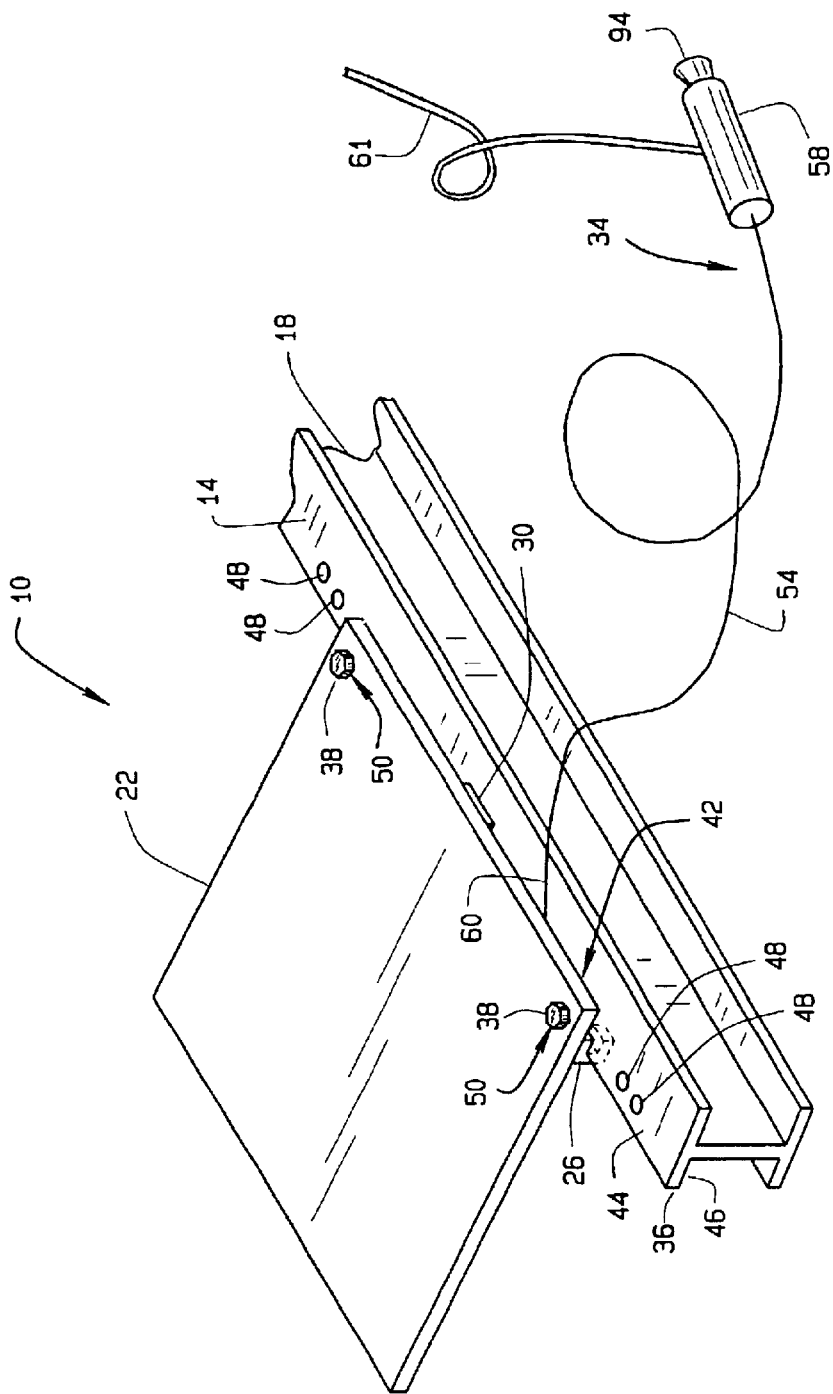
FIG. 1 is a perspective view of a system for inspecting a surface of a floor beam covered by a floor panel, in accordance with a preferred embodiment of the present invention.

FIG. 1 is a perspective view of a system 10, in accordance with a preferred embodiment of the present invention, for inspecting an upper surface 14 of a floor beam 18 covered by a floor panel 22. The term "floor beam" is intended to include any beam or structural member used to support floor panel 22, for example, in the context of aircraft, the term "floor beam" includes aircraft seat tracks.

Inspection system 10 includes at least one nut clip 26, at least one spacer 30 and a micro fiber-optic borescope 34. Nut clip 26 attaches to a floor beam flange 36 and is used to mount floor panel 22 to floor beam 18 utilizing a fastener 38 that couples with nut clip 26. Additionally, nut clip 26 creates a gap 42 between floor panel 22 and beam upper surface 14, Nut clip 26 is described in detail below in reference to FIGS. 2 and 3. Flange 36 includes the beam upper surface 14, a lower surface 46 and a plurality of flange apertures 48 used in mounting floor panel 22 to beam 18.

Each floor panel 22 is coupled to floor beam 18 by attaching a pair of nut clips 26 to floor beam flange 36 such that a panel aperture 50 in each of the two corners along one edge of floor panel 22 align with the nut clips 26 and one of beam apertures 48. Then a fastener 38 is inserted through the panel apertures 50 at each corner of panel 22, through the related flange aperture 48 and threaded into the related nut clip 26. Fastener 38 may comprise any fastener suitable to mount floor panel 22 to beam 18 via nut clip 26, such as a bolt, a screw, or a high lock. Preferably, at least one spacer 30 is installed between floor panel 22 and beam upper surface 14 and positioned between the nut clips 26 at each corner of panel 22, thereby creating gap 42 in the area between nut clips 26. Spacer 30 is described in detail below in reference to FIG. 4.

Micro fiber-optic borescope 34 is a hand held device that includes a micro fiber-optic thread 54 and a borescope viewing device 58. When an imaging end 60 of micro fiber-optic thread 54 is inserted into gap 42, images of beam upper surface 14 are transmitted through micro fiber-optic thread 54 to viewing device 58 where an inspector views the transmitted images. Alternately, micro fiber-optic borescope 34 may include an auxiliary device cable 61 used to connect borescope 34 to peripheral remote devices (not shown) such as a viewing monitor or an image recording device.

Figure 2:
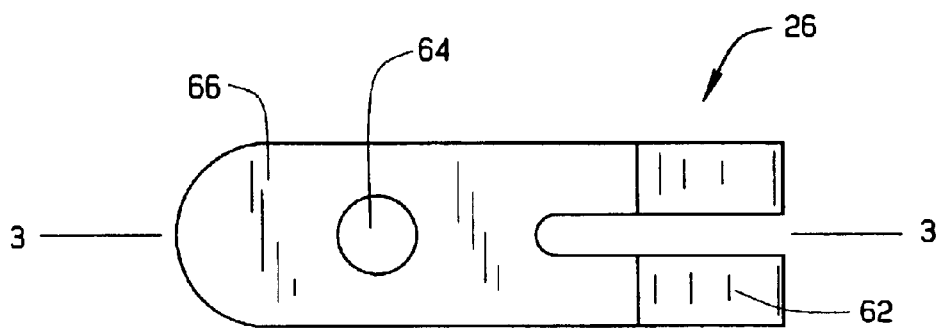
FIG. 2 is a top view of a nut clip included in the system shown in FIG. 1.
Figure 3:
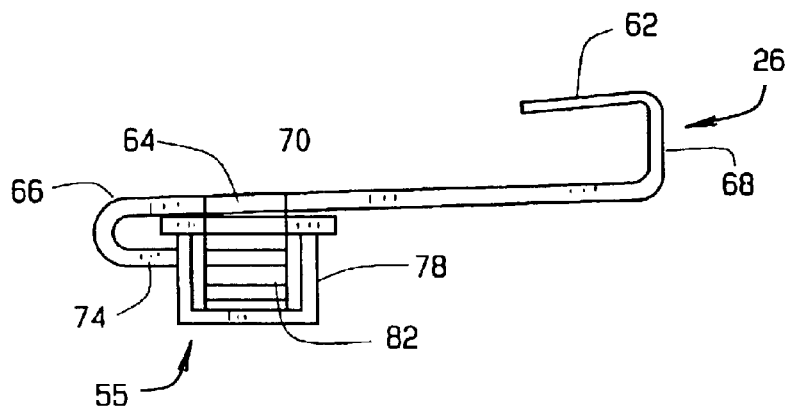
FIG. 3 is cross-sectional side view of the nut clip taken in accordance with section line 3—3 shown in FIG. 2.

Referring to FIGS. 2 and 3, FIG. 2 is a top view of nut clip 26 and FIG. 3 is a cross-sectional side view of nut clip 26 along line 3—3 in FIG. 2. Nut clip 26 includes an upper leg 62, a lower leg 66 that includes a hole 64 and a means 65 for coupling fastener 38 with nut clip 26, and an intermediate section 68 that joins upper leg 62 and lower leg 66. In a preferred embodiment, lower leg 66 includes a first section 70 and a second section 74 that includes the fastener coupling means 65. In this embodiment the fastener coupling means 65 includes a nut housing 78 and a nut 82 enclosed in housing 78. In an alternate embodiment, the fastener coupling means includes a nut attached to lower leg second section 74. In another alternate embodiment, hole 64 is threaded and the fastener coupling means includes threaded hole 64.

Nut clip 26 attaches to floor beam flange 36 by inserting flange 36 between nut clip upper leg 62 and lower leg 66 such that upper leg 62 is in frictional contact with beam upper surface 14, lower leg 66 is in frictional contact with flange lower surface 46, and nut clip hole 64 aligns with one of flange apertures 48. Additionally, upper leg 62 has a shorter length than lower leg 66 such that when nut clip 26 is placed on floor beam flange 36 the aperture 48 that aligns with nut clip hole 64 is free from interference by upper leg 62. Furthermore, nut clip upper leg 62 creates gap 42 in the area adjacent upper leg 62. Thus, by creating gap 42 and keeping flange aperture 48 free from interference, upper leg 62 allows a person inspecting floor beam 18 to insert borescope micro fiber optic thread 54 into gap 42 and view beam upper surface 14 around beam aperture 48, which is an area where corrosion and damage are more likely to occur.

Figure 4:
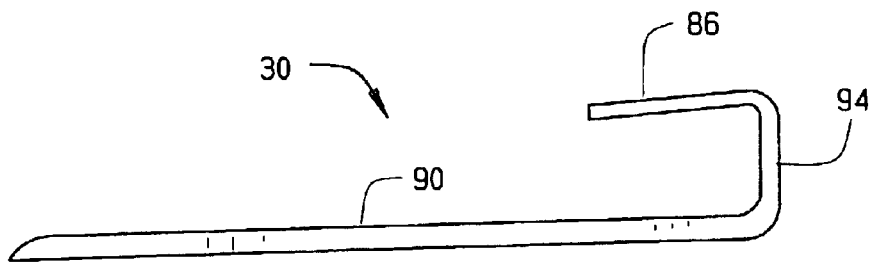
FIG. 4 is perspective view of a spacer included in the system shown in FIG. 1.

FIG. 4 is a perspective view of spacer 30 (shown in FIG. 1), in accordance with a preferred embodiment of the present invention. The preferred embodiment includes at least one spacer 30. However, when a floor panel 22 is relatively small in size, the use of spacer 30 may not be necessary. In the preferred embodiment, spacer 30 includes a first leg 86, a second leg 90 and an intermediate section 94 that joins first leg 86 and second leg 90. For each floor panel 22 coupled to floor beam 18, at least one spacer 30 is attached to beam flange 36 between the nut clips 26 positioned at the two corners along one side of the floor panel 22. Alternately, a plurality of spacers 30 are attached to flange 36 at predetermined intervals between nut clips 26. Spacer 30 attaches to floor beam flange 36 by inserting flange 36 between spacer first leg 86 and second leg 90 such that first leg 86 is in frictional contact with beam upper surface 14 and second leg 90 is in frictional contact with flange lower surface 46.

Additionally, spacer first leg 86 creates gap 42 in the area adjacent first leg 86, thereby allowing a person inspecting floor beam 18 to insert borescope micro fiber optic thread 54 into gap 42 and view beam upper surface 14. Preferably first leg 86 is shorter in length than second leg 90. However, it is envisioned that first leg 86 could alternately have a length, equal to or longer than spacer second leg 90.

In an alternate embodiment spacer 30 comprises a shim that is removably inserted between floor panel 22 and beam upper surface 14 during inspection of floor beam 18. Therefore, when floor beam 18 is to be inspected, spacer 30 is temporarily inserted between floor panel 22 and beam upper surface 14, thereby creating gap 42. After gap 42 is created an inspector can insert micro fiber-optic thread 54 into gap 42 and view upper surface 14 via viewing device 58. Spacer 30 can be any shape suitable to be removably inserted between floor panel 22 and beam upper surface 14 to create gap 42. For example, shim 30 can be rectangular, oval or round, and have a constant thickness or be wedge shaped. Additionally, it is envisioned that spacer 30 may include a handle to aid in its insertion and removal.

In operation, an inspector accesses the floor beams 18 from under the beams 18, for example from the cargo area of an aircraft. The inspector then inserts the imaging end 60 of micro fiber-optic thread 54 into gap 42. Images are transmitted from imaging end 60 through micro fiber-optic thread 54 to viewing device 58. Viewing device then creates high resolution video images of the images received and displays the images on an eye piece viewer 94 (shown in FIG. 1). Thus, using viewing device 58, the inspector views the condition of beam upper surface 14. Alternately, the images can be viewed on a larger viewing screen by connecting micro fiber-optic borescope 34 to the larger viewing screen using auxiliary device cable 61. Additionally, the images of beam upper surface 14 can be recorded by connecting micro fiber-optic borescope 34 to a recording device using auxiliary device cable 61.

By viewing beam surface upper 14 using system 10, an inspector can determine the amount and severity of corrosion or damage occurring to beam 18 without having to completely remove all floor panels 22 and all other structures mounted to floor beams 18 above floor panels 22. Additionally, gap 42 allows corrosion inhibiting compounds to be applied to beam upper surface 14 from below floor beam 18 without removing all the structures mounted to floor beam 18.

While the invention has been described in terms of various specific embodiments, those skilled in the art will recognize that the invention can be practiced with modification within the spirit and scope of the claims.

What is claimed is:

1. A system for inspecting a surface of a support element covered by at least one structure, said system comprising:

at least one clip attached to said support element for attaching said structure to said support element and creating a gap between said structure and said support element, said clip comprising an upper leg and a lower leg including a coupler, said clip being attached to a flange of said support element in a manner whereby said lower leg is in frictional contact with a lower surface of said flange such that said coupler aligns with an aperture in said flange, and said upper leg is in frictional contact with an upper surface of said flange; and a micro fiber-optic borescope for viewing the surface of said support element covered by said structure, via said gap, without removing said structure, wherein said upper leg is configured to have a shorter length than said lower leg such that when said clip is attached to said flange said aperture in said flange is free from interference by said upper leg.

2. The system of claim 1, wherein said system further includes at least one spacer inserted between said support element and said structure for creating said gap between said structure and said support element.

3. The system of claim 2, wherein said spacer comprises a first leg and a second leg, said spacer being attached to said flange such that said first leg is in frictional contact with said lower surface and said second leg is in frictional contact with said upper surface, thereby creating said gap.

4. The system of claim 2, wherein said spacer comprises a shim removably inserted between said support element and said structure.

5. The system of claim 1, wherein said micro fiber-optic borescope comprises a viewing device and a micro fiber-optic thread, said micro fiber-optic thread enabling a user to view said covered support element surface by inserting said micro fiber-optic thread into said gap such that images of the covered support element surface are transmitted, via said micro fiber-optic thread, to said viewing device.

6. The system of claim 1, wherein said gap allows for application of corrosion inhibiting compounds on said support element.

7. A method for inspecting a surface of a support member covered by at least one structure, said method comprising:
attaching the structure to the support member utilizing a clip having an upper leg and a lower leg, the upper leg being shorter than the lower leg;
creating a gap between the support member and the structure utilizing the clip upper leg; and
viewing the support member surface covered by the structure utilizing a micro fiber-optic borescope.

8. The method of claim 7, wherein the support member includes a flange having a lower surface, an upper surface that is covered by the structure, and at least one aperture therethrough, wherein attaching the structure to the support member comprises:
attaching the clip to the flange such that the upper leg of the clip is in frictional contact with the flange upper surface and the aperture is free from interference by the upper leg; and
attaching the clip to the flange such that the lower leg of the clip is in frictional contact with the flange lower surface and a clip lower leg fastener receiver aligns with the aperture.

9. The method of claim 8, wherein the structure includes at least one aperture therethrough, and wherein attaching the structure to the support member further comprises:
passing the fastener through the structure aperture and the flange aperture; and
coupling the fastener with the clip lower leg fastener receiver thereby attaching the structure to the support member such that the clip upper leg creates the gap between the structure and the support member.

10. The method of claim 8, wherein creating a gap between the support member and the structure comprises:
attaching a spacer to the flange such that a first leg of the spacer is in frictional contact with the flange upper surface thereby creating the gap between the support member and the structure; and
attaching the spacer to the flange such that a second leg of the spacer is in frictional contact with the flange lower surface.

11. The method of claim 8, wherein creating a gap between the support member and the structure comprises:
inserting a shim between the support member and the structure to enable viewing the support member surface covered by the structure utilizing a micro fiber-optic borescope; and
removing the shim from between the support member and the structure after viewing the support member surface covered by the structure.

12. The method of claim 7, wherein the micro fiber-optic borescope includes a viewing device and a micro fiber-optic thread, and wherein viewing the support member comprises:
inserting the micro fiber-optic thread into the gap; and
transmitting images of the support member surface covered by the structure to the viewing device, via the micro fiber-optic thread.

13. The method of claim 7, wherein viewing the support member surface comprises applying corrosion inhibiting compounds on the surface of the support member covered by the structure, via the gap.

14. An apparatus for securing panels over an upper surface of a support beam in a manner that permits inspection of said support beam upper surface, comprising:
a plurality of securing clips attached to said support beam for mounting said panels to said support beam; and
at least one spacer positioned separate from said securing clips between said support beam upper surface and said panel for creating a gap between said support beam upper surface and said panel adjacent said spacer sufficient to enable an optical fiber of a viewing device to be inserted therebetween.

15. The apparatus of claim 14, wherein said spacer is secured to said support beam.

16. The apparatus of claim 15, wherein said support beam comprises a flange having an upper surface, an lower surface and an edge, said flange upper surface forming said support beam upper surface, wherein said spacer comprises a clip adapted to be secured on said edge of said flange.

17. The apparatus of claim 16, wherein said spacer is generally U-shaped and includes a first leg engaging said flange upper surface, and a second leg engaging said flange lower surface.

18. The apparatus of claim 14 wherein said spacer comprises a shim removably inserted between said support beam upper surface and said panel.

19. The apparatus of claim 16, wherein said securing clips are generally U-shaped and include a first leg engaging said flange upper surface, and a second leg engaging said flange lower surface, said second leg comprising a coupler for securing a fastener with said securing clip.

20. The apparatus of claim 19, wherein said coupler aligns with an aperture in said flange, and wherein said panels are secured over said support beam outer surface by inserting said fastener through an aperture in said panel and said aperture in said flange and coupling said fastener with said coupler of said securing clip.

21. The apparatus of claim 20, wherein said first leg is shorter than said second leg such that said flange aperture is free from interference by said first leg, and wherein said first leg creates a gap between said support beam upper surface and said panel adjacent said first leg sufficient to enable the optical fiber of the view device to be inserted therebetween.

* * * * *